United States Patent
Casey, II et al.

(10) Patent No.: US 8,579,961 B2
(45) Date of Patent: Nov. 12, 2013

(54) SECTIONAL CRIMPED GRAFT

(75) Inventors: Thomas V. Casey, II, Grafton, MA (US); Kristoff Nelson, Boston, MA (US); Fergus Quigley, Watertown, MA (US)

(73) Assignee: Lifeshield Sciences LLC, Plano, TX (US)

( * ) Notice: Subject to any disclaimer, the term of this patent is extended or adjusted under 35 U.S.C. 154(b) by 1151 days.

(21) Appl. No.: 11/657,140

(22) Filed: Jan. 24, 2007

(65) Prior Publication Data

US 2007/0198079 A1  Aug. 23, 2007

Related U.S. Application Data

(63) Continuation of application No. 10/206,620, filed on Jul. 26, 2002, now abandoned.

(51) Int. Cl.
*A61F 2/06* (2013.01)

(52) U.S. Cl.
USPC .................................. 623/1.28; 623/1.13

(58) Field of Classification Search
USPC ........... 623/1.28, 1.15–1.17, 1.29, 1.31, 1.32, 623/1.52
See application file for complete search history.

(56) References Cited

U.S. PATENT DOCUMENTS

| | | | |
|---|---|---|---|
| 3,878,565 A | 4/1975 | Sauvage | |
| 4,047,252 A | 9/1977 | Liebig et al. | |
| 4,313,231 A * | 2/1982 | Koyamada | 623/1.32 |
| 4,517,687 A * | 5/1985 | Liebig et al. | 623/1.52 |
| 5,282,847 A | 2/1994 | Trescony et al. | |
| 5,476,506 A | 12/1995 | Lunn | |
| 5,697,970 A | 12/1997 | Schmitt et al. | |
| 6,016,810 A | 1/2000 | Ravenscroft | |
| 6,080,198 A | 6/2000 | Lentz et al. | |
| 6,287,335 B1 * | 9/2001 | Drasler et al. | 623/1.28 |
| 6,352,554 B2 | 3/2002 | De Paulis | |
| 7,112,217 B1 * | 9/2006 | Kugler et al. | 623/1.31 |
| 2002/0123790 A1 | 9/2002 | White et al. | |
| 2002/0156522 A1 | 10/2002 | Ivancev et al. | |
| 2003/0017775 A1 | 1/2003 | Sowinski et al. | |

FOREIGN PATENT DOCUMENTS

| | | |
|---|---|---|
| EP | 0 666 066 A1 | 8/1995 |
| EP | 0 943 299 A1 | 9/1999 |
| FR | 2 334 488 | 7/1977 |
| WO | WO 83/03349 | 10/1983 |
| WO | WO 87/05796 | 10/1987 |
| WO | WO 0139700 A1 * | 6/2001 |
| WO | WO02/100454 A1 | 12/2002 |

OTHER PUBLICATIONS

International Search Report mailed on Sep. 5, 2003 in corresponding International Application No. PCT/US03/13103, filed Apr. 29, 2003.

* cited by examiner

*Primary Examiner* — Thomas J Sweet
*Assistant Examiner* — Christopher D Prone
(74) *Attorney, Agent, or Firm* — Vidas, Arrett & Steinkraus (57) ABSTRACT

The present invention provides a sectional crimped graft that allows graft flexibility where required and limits the overall longitudinal extension. The present invention overcomes the disadvantage of fully crimped grafts by controlling the number of crimps per unit length, crimp height, crimp geometry and their location along the graft wall, dependent on the particular end-use application. In so doing, flexibility and elongation can be controllably tailored only in areas where significant anatomical angulation is present. It may also be useful in applications other than stent grafts such as surgical grafts for aortic and peripheral areas. Limiting the overall graft longitudinal extension also facilitates the deployment of the stent-graft into the blood vessel.

18 Claims, 6 Drawing Sheets

SECTIONAL CRIMPED GRAFT

CROSS-REFERENCE TO RELATED APPLICATION

This application is a continuation of U.S. application Ser. No. 10/206,620, filed on Jul. 26, 2002, the contents of which are incorporated herein by reference.

FIELD OF THE INVENTION

The present invention relates generally to a vascular prosthesis for repair or replacement of a blood vessel. More particularly, the present invention provides a sectionally crimped vascular graft for repair of damaged or diseased sections of blood vessels, which can be used alone or in combination with a stent to form a stent-graft device.

BACKGROUND OF THE INVENTION

Vascular grafts are well known to repair or replace the damaged or diseased portions of body vessels such as blood vessels. It has been a common practice to install crimps in a graft by fully crimping the graft. Crimping provides several advantages. For example, textile grafts are much easier for the surgeon to handle once crimped, because crimping provides a self-supporting feature and keeps the lumen of the graft open during implementation. Additional crimping can provide for increased flexibility and longitudinal extension and contraction, where needed. See U.S. Pat. No. 4,047,252 to Liebeg et al. In certain applications, however, flexibility is desired but significant longitudinal extension is not. Additionally, due to the use of stents in combination with grafts as composite devices, the need for full-length crimping to keep the lumen open during implantation is lessened.

In certain applications, such as endoluminal stent-graft devices used in thoracic, abdominal or peripheral applications, it is disadvantageous to have excessive extension subsequent to implantation. Additionally, use of a "fully crimped" graft on a thoracic stent-graft has identified issues with graft elongation within the deployment sheath causing the graft to not fully recover to its original unloaded length. This is particularly apparent when fully crimped grafts are used in devices which allow the flow of arterial blood pressure to be the force which opens the graft lumen. See U.S. Pat. No. 5,697,970 to Schmitt et al. and U.S. Pat. No. 5,476,506 to Lunn. Fully crimped grafts have a significant degree of unwanted elongation extension therefore creating difficulty during deployment. The graft is delivered in the compressed state in an elongated fashion with a stent. The stent can easily return to its original length due to shape memory properties, but the graft cannot. When full graft length recovery is required, herein lies the problem. The graft expands with the stent at each end of the graft, but due to crimping along its entire length, the graft does not recover to its original length during deployment. Thus, prior devices have not provided a solution which balances the need to accommodate vessel angulation flexibility and to facilitate deployment with the need to minimize longitudinal extension.

It is, therefore, desireable to provide a crimped graft which allows flexibility only where needed, i.e., only use crimping where needed, thereby minimizing undesirable longitudinal extension and requiring less recovery during deployment.

SUMMARY OF THE INVENTION

The present invention provides a sectional crimped graft that allows graft flexibility only where required and thus limits the overall longitudinal extension. The present invention overcomes the disadvantage of fully crimped grafts by controlling the number of crimps per unit length, crimp height, crimp geometry and their location along the graft wall. In so doing, flexibility and elongation can be controllably tailored only in areas where significant anatomical angulation is present. It may also be useful in applications other than stent grafts such as surgical grafts for abdominal and peripheral areas. Limiting the overall graft longitudinal extension also enhances the deployment of the stent-graft into the blood vessel.

In accordance with one embodiment of the present invention, crimps are installed only in pre-determined, intermittent locations along the length on the graft. One advantage obtained thereby is to provide needed flexibility to a specific location. Such a graft structure is particularly useful in thoracic stent-graft devices, where a ≥90 degree bend may be present in the treated thoracic aorta. In addition, by minimizing the number of crimps on the graft, the excessive longitudinal extension of the graft is also greatly reduced.

In accordance with another embodiment of the present invention, various factors of crimps on the graft can be varied depending on the desired characteristics for a specific graft application. Such factors are the height of the crimps, the length of the crimped section, i.e., the number of crimps, and the profile, i.e. the cross-sectional geometry of the crimps. The greater the crimp height and the more crimps, the more the elongation of the graft. The elongation can be reduced by reducing the number of crimps per unit length, reducing the height of the crimps and changing their profile. So, depending on the characteristics or diameter of the body or blood vessel, the degree of the crimping can be varied to provide a better fit to the contour of the vessel wall, provide variable flexibility to better accommodate tortuous anatomy, and reduce graft extensioning.

In accordance with further embodiment of the present invention, there is provided a graft having sections of crimps along its full length fully-crimped graft, however the degree of crimping varies upon its length to correspond with expected vascular angulation. Certain sections are individual crimps which do not have a common trough formed by their respective adjacent peaks.

In accordance with even further embodiment of the present invention, a method for producing a graft crimped only partially along its length is provided. The method includes providing an elongate tubular graft having opposing ends defining a fluid passageway therethrough; providing a mandrel comprising individual annular ribs or rings in specific locations; placing a predetermined portion of the graft over the crimp geometry-forming mandrel; applying a mechanical or thermal energy, i.e., mechanical force, fluid pressure, heat, heat and pressure combined, on the predetermined portion to impose the pattern. Desirably, the shape of predetermined portion of the graft is heat-set prior to removing the graft from the mandrel to provide a partially crimped graft product. In one particularly desirable method, the crimps are formed using a heat shrink tube disposed about the graft, which upon subjection to heat shrinks to apply sufficient pressure to the graft such that the crimp geometry is formed in accordance with the underlying mandrel pattern. In a further embodiment, a mechanical roller or similar device is used to impress the graft into the underlying mandrel pattern, thereby forming the mandrel pattern imprint on the graft wall.

In accordance with even further embodiment of the invention, a method of implanting a graft within a body lumen is provided. The method includes providing a longitudinal extending tubular graft having opposing ends with variable crimps located at a predetermined location along a portion of its length and having at least one attachment thereabout to form a stent-graft; delivering the stent-graft to a predetermined position within a body lumen; permitting the graft to radially expand and contact the inner wall of the body lumen. Secondly, the stent-graft has associated with it at least one stent, positioned proximal to the proximal graft end.

DETAILED DESCRIPTION OF THE PREFERRED EMBODIMENT

Figure 1:
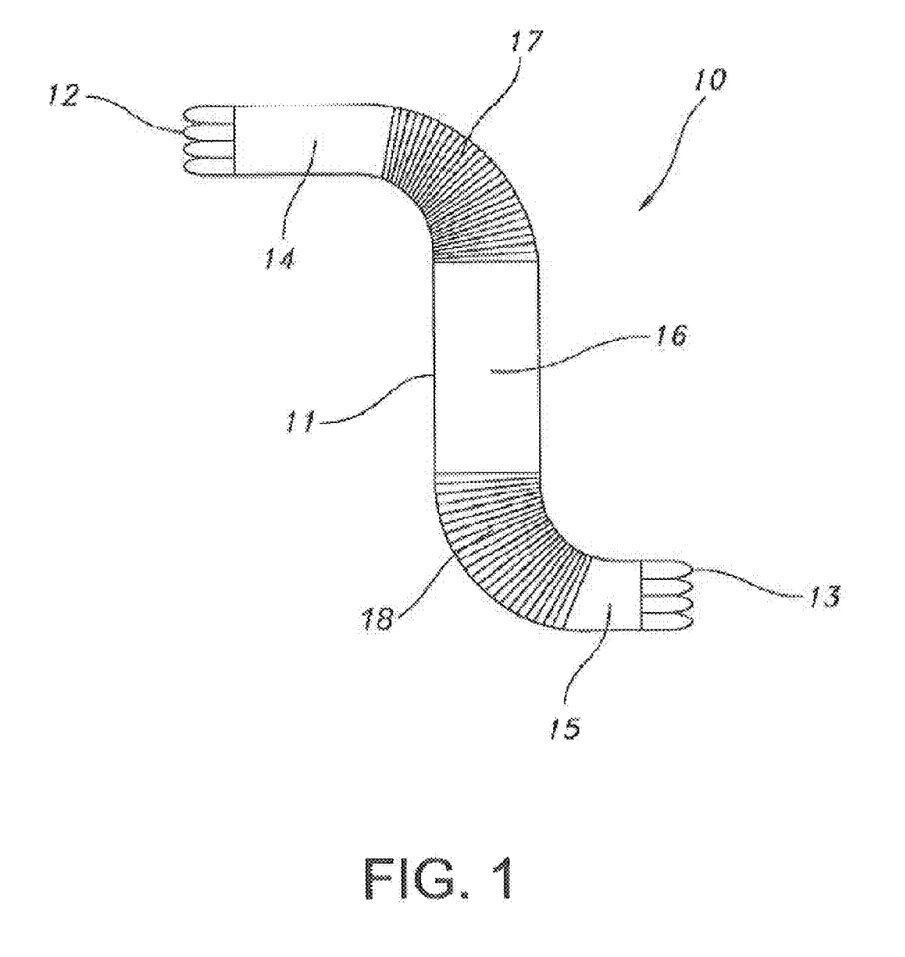
FIG. 1 is an illustration of crimps installed in specific areas of the graft of the present invention.

Referring now to FIG. 1, one aspect of the present invention is provided. Stent-graft 10 is an elongate generally tubular body, desirably a thin walled hollow cylinder 11 having opposed-stent ends, a first open-stent end 12 and a second open end 13. The graft is divided into end portions 14 and 15 adjacent open-stent ends 12 and 13, respectively. The graft 10 has central portion 16 extending longitudinally between the end portions 14 and 15.

Crimps 17 are incorporated in graft 10, extending from the first end portion 14 towards the central portion 16. Crimps 17 are incorporated on the other side of the graft extending from the second end portion 15 towards the central portion 16. Crimping in the manner shown in FIG. 1 is one example of crimping only on those areas of the graft where flexibility is required. In FIG. 1, the flexibility is needed on the portion that is to be bent or used at a particular angle or curvature. Since this type of flexibility is not required on other portions of the graft, the rest of the graft need not be crimped, avoiding excessive longitudinal graft extension. Alternatively the reduction in crimping height or number of crimps along the graft length also reduces excessive extension of the graft. Limiting the overall graft longitudinal extension facilitates the deployment of catheter into the blood vessel by reducing the potential for graft catching a stent frame. Moreover, because the graft may be used with a stent to form a stent-graft device, crimps along the full length of the graft for the purpose of facilitating handling by the surgeon is not necessary.

Figure 2:
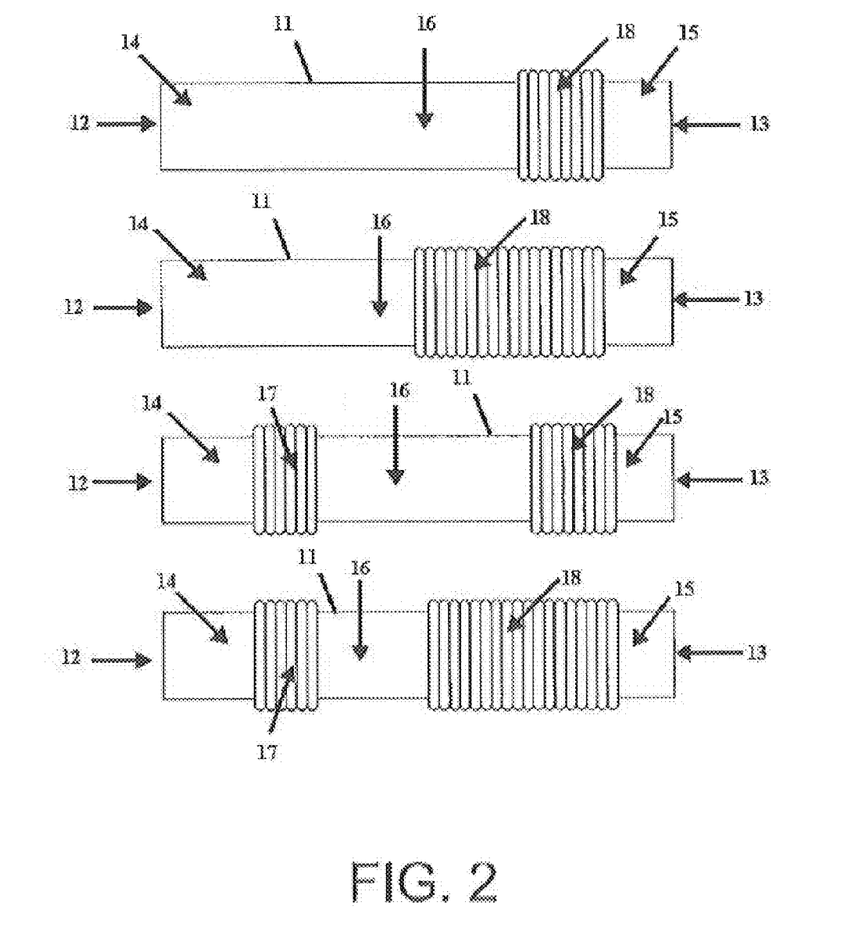
FIG. 2 is an illustration of various sectional crimp grafts with uniform crimp height of the present invention.

It is to be understood that while the exemplified embodiment has been illustrated with specific geometry, a wide variation is possible within the broad teachings of this invention. A few examples of variations of crimping are illustrated in FIG. 2. FIG. 2 shows several of many possible sectional crimped graft designs with uniform crimp heights, simply illustrating that flexibility to compress and expand has been provided only where needed and minimizing the longitudinal extension.

Figure 3:
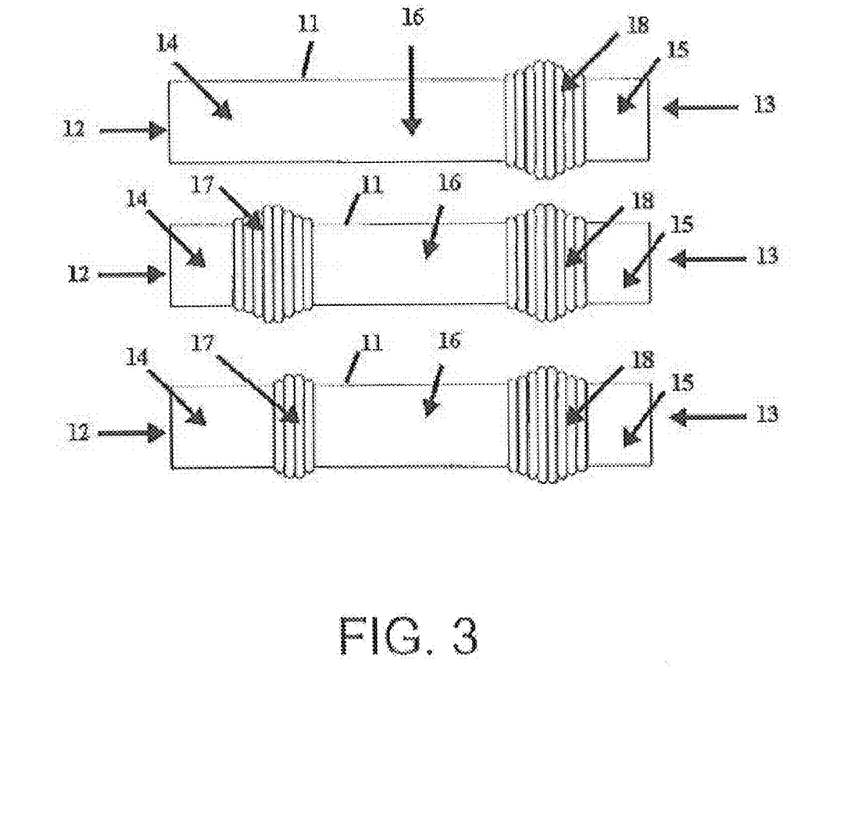
FIG. 3 is an illustration of various sectional crimp grafts of variable crimp heights of the present invention.

Moreover, the height and linear density of the crimps may be varied depending on the desired characteristics for a specific graft application. FIG. 3 shows several non-limiting designs of variable crimp-heights in accordance with the present invention. The advantages to varying the height are that it minimizes excessive longitudinal graft extension and at the same time provides variable flexibility to better negotiate difficult anatomical bends. Height also determines degree of elongation.

The diameter of the grafts of the present invention may preferably be between the ranges of 3-48 mm. The frequency/length, i.e., number of crimps per a given length may vary. For example, about 1 to about 42 crimps per cm may be employed. Desirably about 6 to about 12 crimps per cm may be employed. The height of the crimps may be in the range of 0.5-1.5 mm, preferably between 0.25-0.5 mm. The length of the crimps along the graft may be in the range of 5 mm-200 mm preferably between 20 mm-150 mm. The spacing between the crimps may preferably be in the range of anywhere from 1 mm to 100 mm preferably between 10 mm-30 mm.

Figure 4A:
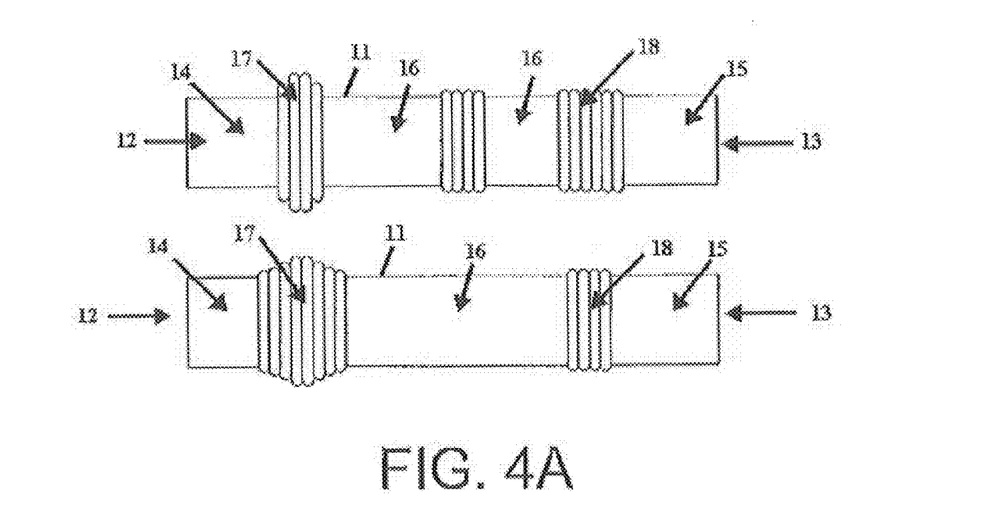
FIG. 4 is an illustration of various combinations of sectional crimp grafts with varying crimp amplitude, frequency and profile in accordance with the present invention.

FIG. 4a shows combinations of sectional crimp grafts designs with several varying factors of the crimps on the graft. Such designs include crimps having variable and uniform crimp height, variable number of crimps per unit length, thereby illustrating that any combination of the graft designs is possible depending on the flexibility required to negotiate tortuous anatomical bends, while minimizing elongation.

Figure 4B:
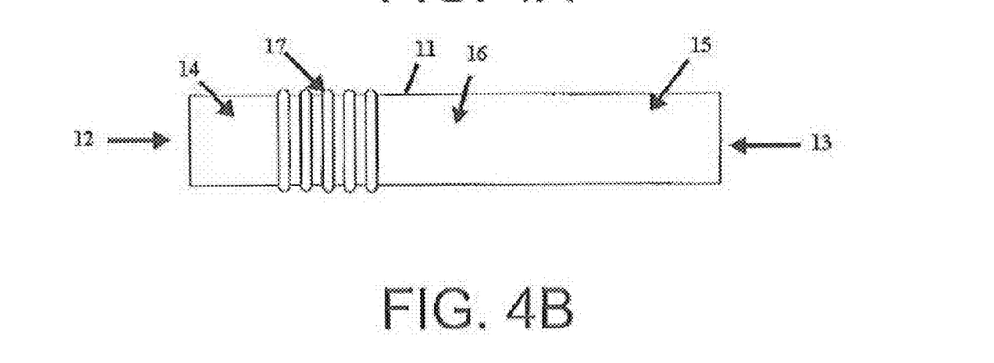

FIG. 4b illustrates a sectional crimp graft design with separate individual crimps with spaces between each other. Certain sections are individual crimps which do not have a common trough formed by their respective adjacent peaks. Again, this particular graft design portrays that the degree or level of flexibility can be varied based on the physical characteristics of the damaged or diseased portion of the blood vessel.

Figure 5:
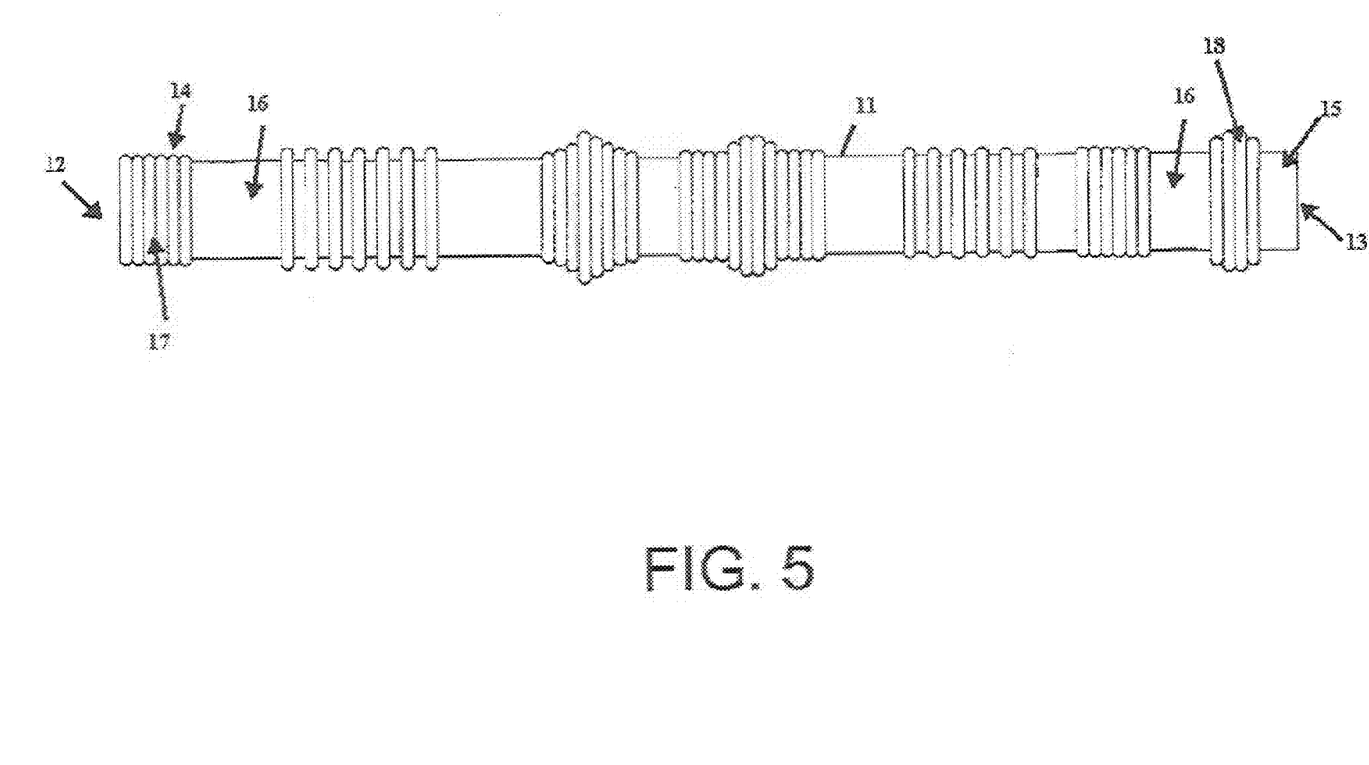
FIG. 5 is an illustration of a graft having sections of crimps along its full length in accordance with the present invention. Certain sections are shown where individual crimps do not have a common trough formed by their respective peaks.

FIG. 5 shows a graft having sections of crimps along its full length fully crimped graft in accordance with a preferred embodiment of the present invention. The degree of crimping varies upon its length to correspond with expected vascular angulation. For instance, crimps may be of uniform and variable height and length. The crimps may also preferably be individual crimps spaced apart from each other which do not have a common trough formed by their respective adjacent peaks.

Having described the sectional crimped graft of the present invention, its construction and manufacture will now be discussed. As noted, the grafts of the present invention may be constructed of a variety of materials. Such materials may be in form of films and yarns, woven, knitted, braided or extruded material. Textile materials are specifically useful in vascular graft applications, in that textile pattern of the material can be constructed to be very thin and pliable and also capable of permitting sufficient ingrowth of surrounding tissue, while also being capable of maintaining a fluid-tight, i.e. low porosity blood-tight wall structure. The textile graft is desirably a woven material, and can be flat woven using any known weave pattern. The wall of the graft may be any conventional useful thickness, for example, 0.10 mm to about 0.75 mm, but is desirably no greater than about 1.0 mm. Moreover, any type of textile material suitable for use in the body can be used as the yarns or fibers of the present invention. Synthetic materials include a variety of polymers including, but not limiting to, polyesters, polypropylenes (PP), polyethylenes (PE), polyurethanes (PU), polytetrafluoroethylenes (PTFE) and mixtures thereof. Polyethylene terephthalate (PET) is particularly useful.

Woven tubular textile products are particularly useful in manufacturing vascular grafts in variety of shapes and sizes. After the graft is woven, a predetermined portion of the graft may then be subjected to one or more crimping process. In one aspect of the invention the graft is placed on a mandrel having a grooved or corrugated surface therein. The grooved surface is a series of individual annular ribs or rings in specific locations. These ribs or rings supply the template by which the crimps in the graft wall are formed. The predetermined portion of the graft is then placed over the crimp geometry forming mandrel and forced into the groove by mechanical or fluid force and cause the graft wall to assume the mandrel's groove shape, thereby forming annular crimps in the graft wall. The graft may preferably be heated to set the desired crimp pattern, which maybe varying from about 10 to 30 crimps per inch of longitudinal graft length. Alternate such grooves or crimps are shown in U.S. Pat. Nos. 5,697,970 and 5,476,506, the contents of all of which are incorporated herein by reference.

The amplitude (height) of the crimping and the number of crimps is determined based on the body lumen be longitudinally stretched so as to conform to that portion of the body lumen. The degree of crimping is varied in the graft to accommodate the curvature in the aortic arch ranging from about 30° to about 180° angles. The specific portions of the graft to be crimped are also chosen. For instance, if in using the graft a ≥90 degree angulation is anticipated, crimping need only be incorporated on that portion of the graft where the bending will take place, providing greater flexibility only where required. In other words, crimping is formed only as required at portions of the graft to yield flexibility with conformance to the body. Crimping is also formed as required to provide longitudinal extension to permit loading of the graft for delivery as will be described in detail below.

Figure 6:
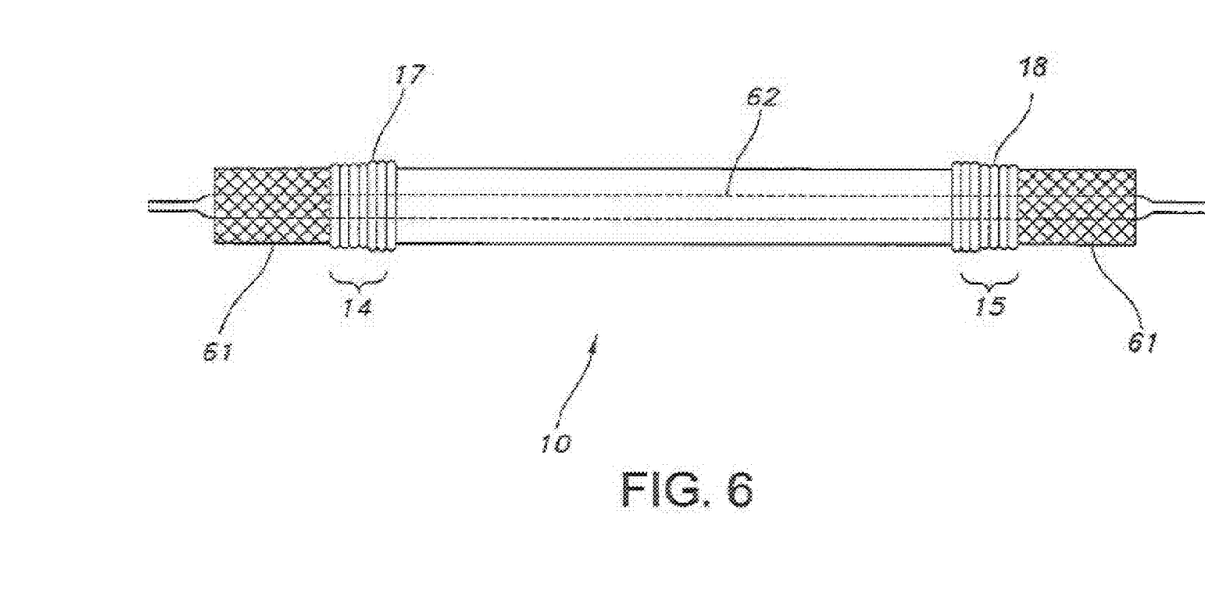
FIG. 6 is an illustration of stent-graft assembly for implantation within a body lumen.

Referring to FIG. 6, illustrated therein schematically is a stent-graft of the present invention at a preloaded stage for deployment into a vascular vessel. Stent 61 is disposed within and preferably attached to end portions 14 and/or 15 of graft 10. A stent 61 can alternatively be constructed as lining within a graft (not shown) extending from one end of the graft to the other to provide both fastening of the graft to the stent and additionally structural stability.

The partially crimped graft of the present invention, graft 10, preferably with the end portions 14 and 15 affixed to stent 61, is positioned on a catheter 62 to be delivered endoluminally. During delivery or deployment, the stent-graft 10 stretches longitudinally to provide an open lumen and maintains its flexibility. As opposed to fully crimped grafts, which do return to their original length, the grafts of the present invention more readily return to their original length, thereby permitting longitudinal flexibility where required, while maintaining structural integrity for long term patency. For example, graft's original length will be at 100% at a relaxed state, which is the pre-loaded stage, as shown in FIG. 6. Upon delivery of the prostheses, i.e. stent-graft assembly, the graft's length may stretch longitudinally, in the range of 150%-250% and then once the graft is delivered within the body vessel, it is released, preferably the graft's length will come back to its original position, which may vary up to 100% of its original length.

Various methods of deployment of the graft of the present invention into a vascular vessel of a patient. One such method is by mounting the stent-graft device on a balloon catheter. The balloon is then expanded to expand the stent, and trap and/or sandwich the end portions of the graft between the expanded stent and the wall of the healthy portion of the vessel. Then the balloon is deflated and catheter removed from the patient, thereby releasing said stent-graft assembly in place.

Another method is due to the utilization of self-expanding stents which are generally made of nitinol, which has the ability to perform well while both in spring-like mode, as well as in a memory mode based on temperature and processing. A stent is disposed within the graft, preferably at the open ends of the graft. The self-expanding stents which have spring-like action will cause the stent to radially expand or stents which expand upon increase in temperature due to the memory imparted properties of the stent material, such as nitinol. When such self-expanding stent-graft is deployed within the blood vessel, the stent expands so as to expand the graft into contact with the lumen to be repaired, and further securely anchor the graft in place to prevent the movement of the prosthesis once properly implanted.

Another method is the utilizing of a sheath. The graft/stent assembly is disposed within a tubular sheath having a longitudinal bore, which holds the graft and stents in a compressed condition so that it may be smoothly delivered intraluminally via the delivery catheter. Once properly located, the sheath is retracted and the graft is removed from the sheath, which permits the stents to expand, thereby opening the graft so it substantially conforms to the interior wall of a lumen.

The stent may be made from a variety of materials including stainless steel, titanium, platinum, gold and other biocompatible metals. Thermoplastic materials which are inert in the body may also be employed. Alternatively, thermoplastic materials that exhibit known controlled degradation (biodegradable) are useful stent materials. Shaped memory alloys having super elastic properties generally made from specific ratios of nickel and titanium, commonly known as nitinol, are among the preferred stent materials.

Various stent types and stent constructions may be employed in the invention. Among the various stents useful include, without limitation, self-expanding stents and balloon expandable extents. The stents may be capable of radially contracting, as well and in this sense can best be described as radially distensible or deformable. Self-expanding stents include those that have a spring-like action which causes the stent to radially expand, or stents which expand due to the memory imparted properties of the stent material for a particular configuration at a certain temperature. Nitinol is one material which has the ability to perform well while both in spring-like mode, as well as in a memory mode, based on temperature and processing. Other materials are of course contemplated, such as stainless steel, platinum, gold, titanium algiloy and their combinations (e.g.: gold coat, sterling silver, or gold/platinum cored nitinol, and other biocompatible metals, as well as polymeric stents).

The configuration of the stent may also be chosen from a host of geometries. For example, wire stents can be fastened into a continuous helical patterns, with or without a wave-like or zig-zag in the wire, to form a radially deformable stent. Individual rings or circular members can be linked together such as by struts, sutures, welding or interlacing or locking of the rings to form a tubular stent. Tubular stents useful in the present invention also include those formed by etching or cutting a pattern from a tube. Such stents are often referred to as slotted stents. Furthermore, stents may be formed by etching a pattern into a material or mold and depositing stent material in the pattern, such as by chemical vapor deposition or the like.

Moreover, it is anticipated that graft 10 can be partially or wholly coated with natural coatings, or synthetic coatings, hydrophilic or drug delivery-type coatings which facilitate long-term healing of diseased vessels. Such a coating is preferably bioabsorbable, and is preferably a therapeutic agent or drug, including, but not limited to, anti-thrombogenic agents (such as heparin, heparin derivatives, urokinase, and PPack (dextrophenylalanine proline arginine chloromethylketone)); anti-proliferative agents (such as enoxaprin, angiopeptin, or monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasalazine, and mesalamine); antineoplastic/antiproliferative/anti-miotic agents (such as paclitaxel, 5-fluorouracil, cisplatin, vinblastine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethyl keton, an RGD peptide-containing compound, heparin, antithrombin compounds, platelet receptor antagonists, anti-thrombin antibodies, anti-platelet receptor antibodies, aspirin, prostaglandin inhibitors, platelet inhibitors and tick antiplatelet peptides); vascular cell growth promotors (such as growth factor inhibitors, growth factor receptor antagonists, transcriptional activators, and translational promotors); vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin); cholesterol-lowering agents; vasodilating agents; and agents which interfere with endogenous vascoactive mechanisms. While the foregoing therapeutic agents have been used to prevent or treat various conditions, they are provided by way of example and are not meant to be limiting, as other therapeutic drugs may be developed which are equally applicable for use with the present invention.

While the invention has been described by the foregoing detailed description and the drawings in relation to the preferred embodiments, it will be understood by those skilled in the art that various changes may be made without deviating from the spirit and scope of the invention.

What is claimed is:

1. An implantable tubular graft for placement in a body vessel having at least a first curved location, a second curved location, and a non-curved location, the tubular graft comprising:
   a generally tubular graft body having a tubular wall including first and second opposite open ends and a varying outer diameter, said tubular wall comprising:
   a first portion comprising at least a first circumferential, radially outward projecting crimp, the first circumferential, radially outward projecting crimp having a first length and a first outer diameter;
   a second portion comprising at least a second circumferential, radially outward projecting crimp, the second circumferential, radially outward projecting crimp having a second length and a second outer diameter; and
   an uncrimped portion disposed between the first circumferential, radially outward projecting crimp and the second circumferential, radially outward projecting crimp for placement at said non-curved location of said body vessel, the un-crimped portion having a third outer diameter less than each of the first outer diameter and the second outer diameter,
   wherein the first crimp projects outward beyond the uncrimped portion and the second crimp projects outward beyond the uncrimped portion and the first outer diameter is substantially the same as the second outer diameter.

2. The tubular graft of claim 1, wherein said first and second circumferential, radially outward projecting crimps include crimps generally in a wave-like pattern.

3. The tubular graft of claim 1, wherein said at least a first circumferential, radially outward projecting crimp includes a plurality of crimps of uniform length.

4. The tubular graft of claim 1, wherein said first circumferential, radially outward projecting crimp includes crimps of variable length.

5. The tubular graft of claim 1, wherein said at least a first circumferential, radially outward projecting crimp includes a plurality of crimps of uniform height.

6. The tubular graft of claim 1, wherein said first circumferential, radially outward projecting crimp includes crimps of variable height.

7. The tubular graft of claim 1, wherein said first circumferential, radially outward projecting crimp includes crimps not sharing a common trough formed by adjacent peaks.

8. The tubular graft of claim 1, wherein the first circumferential, radially outward projecting crimp is located proximal to the first open end.

9. The tubular graft of claim 1, wherein at least one said open end is mounted over an expandable stent.

10. The tubular graft of claim 9, wherein said graft and expandable stent are loaded in a catheter.

11. The tubular graft of claim 1, wherein the entire tubular graft is mounted over an expandable stent.

12. The tubular graft of claim 1, wherein both of said at least a first circumferential, radially outward projecting crimp and said at least a second circumferential, radially outward projecting crimp has a crimp-to-length ratio between about 1 crimp/cm and about 42 crimps/cm.

13. The tubular graft of claim 12, wherein the crimp-to-length ratio is between about 6 crimps/cm and about 12 crimps/cm.

14. The tubular graft of claim 1, wherein the uncrimped portion has a uniform diameter from the first crimp to the second crimp.

15. The tubular graft of claim 1, wherein the first outer diameter is the same as the second outer diameter.

16. A method of implanting a graft device for placement in a body vessel having at least two curved locations and a non-curved location, comprising:
   providing an implantable tubular graft comprising a generally tubular graft body having a tubular wall including first and second opposite open ends and a varying outer diameter, said tubular wall comprising: a first portion comprising at least a first circumferential, radially outward projecting crimp, the first circumferential, radially outward projecting crimp having a first length and a first outer diameter; a second portion comprising at least a second circumferential, radially outward projecting crimp, the second circumferential, radially outward projecting crimp having a second length and a second outer diameter; and an uncrimped portion disposed between the first circumferential, radially outward projecting crimp and the second circumferential, radially outward projecting crimp for placement at said non-curved location of said body vessel, the un-crimped portion having a third outer diameter less than each of the first outer diameter and the second outer diameter, wherein the first crimp projects outward beyond the uncrimped portion, the second crimp projects outward beyond the uncrimped portion and the first outer diameter is substantially the same as the second outer diameter;
   positioning the graft device about a catheter;

deploying said graft within said body vessel such that each of said circumferential, radially outward projecting crimps is placed at a curved location of said body vessel; and allowing said graft to radially expand to contact a body lumen wall, wherein said uncrimped portion is disposed between said circumferential, radially outward projecting crimps.

17. The method of claim 16, further comprising positioning a stent about at least a portion of the graft to form a graft device; said stent and graft being in a longitudinally stretched low profile state for insertion into the body, thereby increasing the original length of the graft.

18. The method of claim 17, further comprising deploying said graft to permit radial expansion and to bring the graft to its approximate original length.

* * * * *